United States Patent [19]
Feller et al.

[11] Patent Number: 5,654,554
[45] Date of Patent: Aug. 5, 1997

[54] METHOD AND APPARATUS FOR THE RECORDING OF PROPERTIES ON ELONGATE BODIES

[75] Inventors: Peter Feller, Benglen; Hans Wampfler, Zürich, both of Switzerland

[73] Assignee: Zellweger Luwa AG, Uster, Switzerland

[21] Appl. No.: 562,847

[22] Filed: Nov. 27, 1995

[30] Foreign Application Priority Data

Nov. 29, 1994 [CH] Switzerland ............... 03599/94

[51] Int. Cl.$^6$ ........................................... G01N 21/86
[52] U.S. Cl. ...................... 250/559.45; 250/559.46; 356/240
[58] Field of Search ................... 250/559.46, 559.45, 250/559.48, 559.32, 223 R; 356/237, 430, 238, 240

[56] References Cited

U.S. PATENT DOCUMENTS

| | | | |
|---|---|---|---|
| 3,717,711 | 2/1973 | Abilock et al. | 356/238 |
| 3,786,265 | 1/1974 | Abilock et al. | 250/559.47 |
| 4,539,561 | 9/1985 | Wulff | 340/675 |
| 4,705,957 | 11/1987 | Puffer et al. | 250/559.45 |
| 5,030,841 | 7/1991 | Wampfler | 356/429 |
| 5,050,437 | 9/1991 | Etter | 73/830 |
| 5,054,317 | 10/1991 | Laubscher | 73/160 |
| 5,130,557 | 7/1992 | Kettl | 250/559.43 |
| 5,178,008 | 1/1993 | Aemmer | 73/160 |

FOREIGN PATENT DOCUMENTS

| | | |
|---|---|---|
| 0 335 155 | 10/1989 | European Pat. Off. . |
| 0 241 894 | 8/1990 | European Pat. Off. . |
| 0 578 975 | 6/1993 | European Pat. Off. . |
| 2192722 | 11/1990 | United Kingdom . |

OTHER PUBLICATIONS

Panasonic, Industrie Video Systeme, Advertisement.
Scanner News, Issue #7, Apr. 1993, p. 1.
Imaging Technology Inc.; pp. 36–37, 47–50.

*Primary Examiner*—Que Le
*Attorney, Agent, or Firm*—Burns, Doane, Swecker & Mathis, LLP

[57] ABSTRACT

The invention relates to a method and apparatus in which an elongated body (1) such as a yarn, a roving or a band, is measured continuously by means of a simple cost-effective sensor (5). A further, more complicated sensor (8) which works more accurately but more slowly is triggered by the simpler sensor if the latter indicates special events. These events are then stored by the complicated sensor and are subsequently analyzed accurately in a greater amount of time. The entire time span occurring between two special events can be utilized for this analysis.

9 Claims, 7 Drawing Sheets

METHOD AND APPARATUS FOR THE RECORDING OF PROPERTIES ON ELONGATE BODIES

FIELD OF THE INVENTION

The invention relates to apparatus for the recording of characteristic properties on an elongate body which is moved in the longitudinal direction and which is recorded by means of a sensor. By "elongate bodies" are to be understood, for example, textile yarns, ropes, wires, bands, etc.

BACKGROUND OF THE INVENTION

Known devices make it possible, by means of suitable sensors, to measure a wide variety of properties on, for example, a continuously moved yarn. Since the aim is to achieve increasingly higher outputs, the tendency is to produce or test the yarn more rapidly. The yarn is therefore also to pass more rapidly through subsequent processing stages or tests in the laboratory. At high speeds, it becomes increasingly more difficult for conventional sensors to record even irregularities of small extent reliably on the running yarn. The quality of recording of the individual irregularities is therefore impaired.

To raise the monitoring quality, it is conceivable to employ sensors which can supply more comprehensive information on irregularities. One example of such a sensor is a television camera with following image processing which, indeed, not only makes the irregularity recognizable per se, but can also give particulars on the nature of the irregularity. However, for a fast-running yarn which is moved at a speed of 400 m/min and which is recorded by a television camera working at a clock frequency of 50 Hz, this means that the recorded fields show yarn portions which are 130 mm apart. Reckoning on a field resolution of 160 lines, this results in a resolution limit of 0.8 mm on the yarn. This is insufficient for exact analysis of the yarn. If a special camera with a higher frame rate is used, the resolution limit is thereby improved, but the computing complexity during image processing also rises considerably as a result. The sufficiently high-performance special hardware necessary for this purpose must be aimed at the immediate problem to be observed, which also means that this hardware is inflexible. This difficulty could be overcome by no longer aiming to ensure uninterrupted monitoring of the yarn. In that case, although there is very good recording of the yarn properties on specific portions, there is nevertheless no longer any monitoring at all on other portions.

SUMMARY OF THE INVENTION

The present invention provides a method and a device, by means of which a fast-running yarn can be monitored in terms of particular properties uninterruptedly and with very high resolution.

According to an aspect of the invention, this is obtained by the use of two different and interconnected sensors, a first sensor monitoring the yarn continuously for particular properties and, when specific events occur, activating the second sensor which, for a limited time, monitors the yarn more accurately for further properties. Such a device could comprise, for example, an optically or capacitively working first sensor and a second sensor designed as a television camera. However, other combinations of two sensors, which work on different measurement principles, are also conceivable, for such a combination can, indeed, take into account expressly the properties to be investigated and be designed in such a way that the properties sought are recorded in an optimum manner.

The advantages afforded by the device are to be seen, in particular, in that, on the one hand, the properties to be recorded can be recorded in an optimum manner and be represented with any accuracy, and in that, on the other hand, the evaluation of the data occurring is simplified, in that care is taken to ensure that the quantity of data occurring is restricted. Consequently, the results can also be output quickly and are therefore available virtually immediately after the recording. Furthermore, by a skillful and exactly problem-related selection and combination of the sensors, an optimum recording of any properties or data of a fast-running yarn can be ensured.

BRIEF DESCRIPTION OF THE DRAWINGS

The invention is explained in more detail below by means of examples and with reference to the accompanying drawings, in which.

DETAILED DESCRIPTION OF PREFERRED EMBODIMENTS

Figure 1:
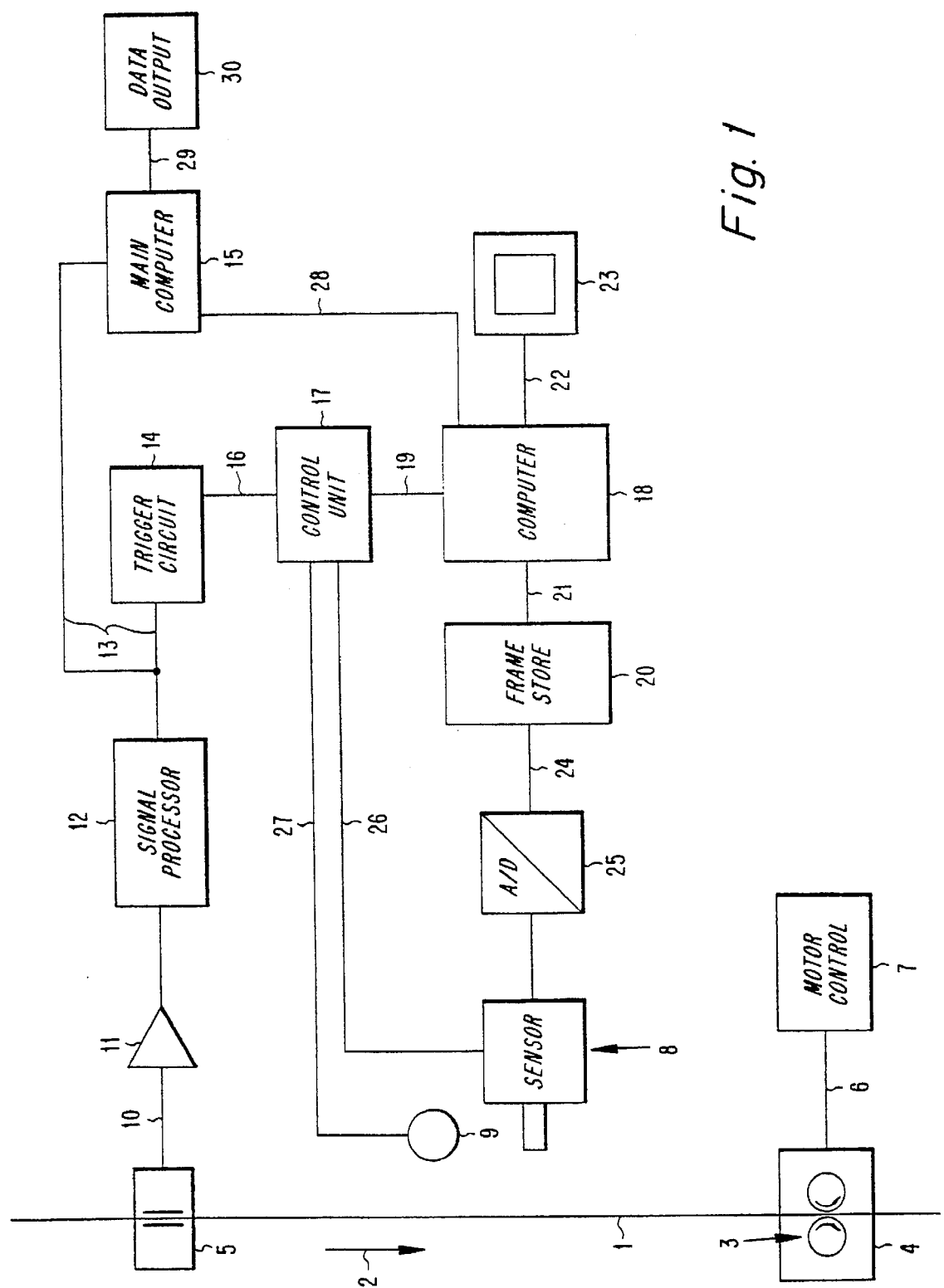
FIG. 1 shows a diagrammatic representation of a first embodiment.

FIG. 1 shows a first example of a device according to the invention. In it can be seen an elongate body 1 which can take the form, for example, of yarn, roving, band, optical fibre, rope, cable, tube, etc. which is moved in the direction of an arrow 2 by being drawn by drive rollers 3 of a drive device 4 and, at the same time, is also recorded by a sensor 5 which is represented here as a capacitively working sensor. The drive device is connected to a motor control 7 via a line 6. A further sensor 8, represented here as a television camera, is set up in the region of the body 1 in such a way that it can reproduce an optimum image of the body 1. Also optionally provided in addition is a lighting unit 9 which lights the body at a time and in a region to be reproduced in the image.

The sensor 5 is connected via a line 10 to a signal amplifier 11 and to a signal-processing unit 12. Where yarns are concerned, these elements together form a yarn tester of a type known per se and disclosed, for example, in U.K. Patent No. 2,192,722, the disclosure of which is incorporated herein by reference in its entirety. The signal-processing unit 12 processes the arriving signals, for example by comparing the arriving values with predetermined values which make it possible to differentiate between admissible (acceptable) values and inadmissible (unacceptable) values, thereby making it possible to decide whether a value is admissible (acceptable) or not.

The signal-processing unit is also connected via lines 13 to a trigger circuit 14 and a main computer 15. The latter, on the basis of the program loaded in it, controls the cycles in the individual elements of this device by instructing the latter at the right time to perform the respective functions. The trigger circuit 14 converts the signals from the signal-processing unit 12 into corresponding control signals for the further sensor 8 and, for this purpose, is connected via a line 16 to a control unit 17 for the further sensor 8, the said control unit 17 itself being connected via a line 19 to a computer 18. The latter is connected, on the one hand, via a bus 21 to frame store 20 and, on the other hand, via a line 22 to a video display as an output unit 23. The frame store 20 is connected to the sensor 8, that is to say, here, the camera, via a bus 24 and via an analog/digital converter 25. Further connections 26 and 27 are provided between the control unit 17 and the sensor 8, on the one hand, and the lighting unit 9, on the other hand. Furthermore, connections 28 and 29 connect the main computer 15 to the computer 18 and to a data output unit 30, here, for example, a printer. Either a matrix camera or a line-scan camera can be provided as the sensor 8. Suitable matrix cameras may, for example, use image sensors (particularly area scan image sensors such as those offered under the trademark MEGASENSOR) from Dalsa, Inc., as indicated on page 1 of the April 1993 issue of Scanner News, the disclosure of which is incorporated herein by reference. Suitable line-scan cameras also are available commercially, for example, from Panasonic Video Systems. Two frame stores 20 are preferably provided, so as always to have one frame store free for new data, whilst the other store can contain the data to be evaluated.

The device apparatus according to FIG. 1 is suitable, for example, for examining a yarn for the quantity and nature of neps. The neps form thickened points in the yarn 1 which are recorded or sensed by the sensor 5. Depending on the presettings made and stored in the signal-processing unit 12, all the neps or only particularly large neps are separated out for closer consideration by the sensor 8. Once a nep has been selected by the signal-processing unit 12 (which can also be interpreted as part of the sensor), the trigger circuit 14 actuates the control circuit 17 for the sensor 8, the said control circuit 17 ensuring that the sensor 8 and the lighting unit 9 are activated after a time delay corresponding to a distance between the sensors 5 and 8. The signals which the sensor 8 transmits, in this case the images from the camera, are digitized in the A/D converter 25 and are subsequently stored in the frame store 20. These images can then be evaluated directly on the video display 23 by persons viewing them or the images can be further processed in the computer 18, for example by being compared with the patterns stored there and by transmitting for viewing only an image of the differences from the pattern. Or the computer measures the extent of the neps and outputs these measured values simultaneously. Instead of an output of exact dimensions of the neps, the computer 18 can also assign the neps to a predetermined class which groups together similar or identical neps. The computer 18 can then simply carry out a more precise classification or also take into account new characteristic values. The computer 18 can also perform a simulation of a fabric which would be obtained from the yarn having these neps, as is known from European Patent Application No. 0,578,975, the disclosure of which is incorporated herein by reference.

The nappiness or hairiness of yarn can be investigated in a similar way by means of the device according to FIG. 1. In that case, the sensor 5 is designed as a nappiness or hairiness sensor and signals places of special nappiness, possibly so-called nests of nappiness, that is to say places where the yarn has a particularly large amount of nap. Such places can be examined more accurately in the sensor 8, here likewise a camera.

Figure 2:
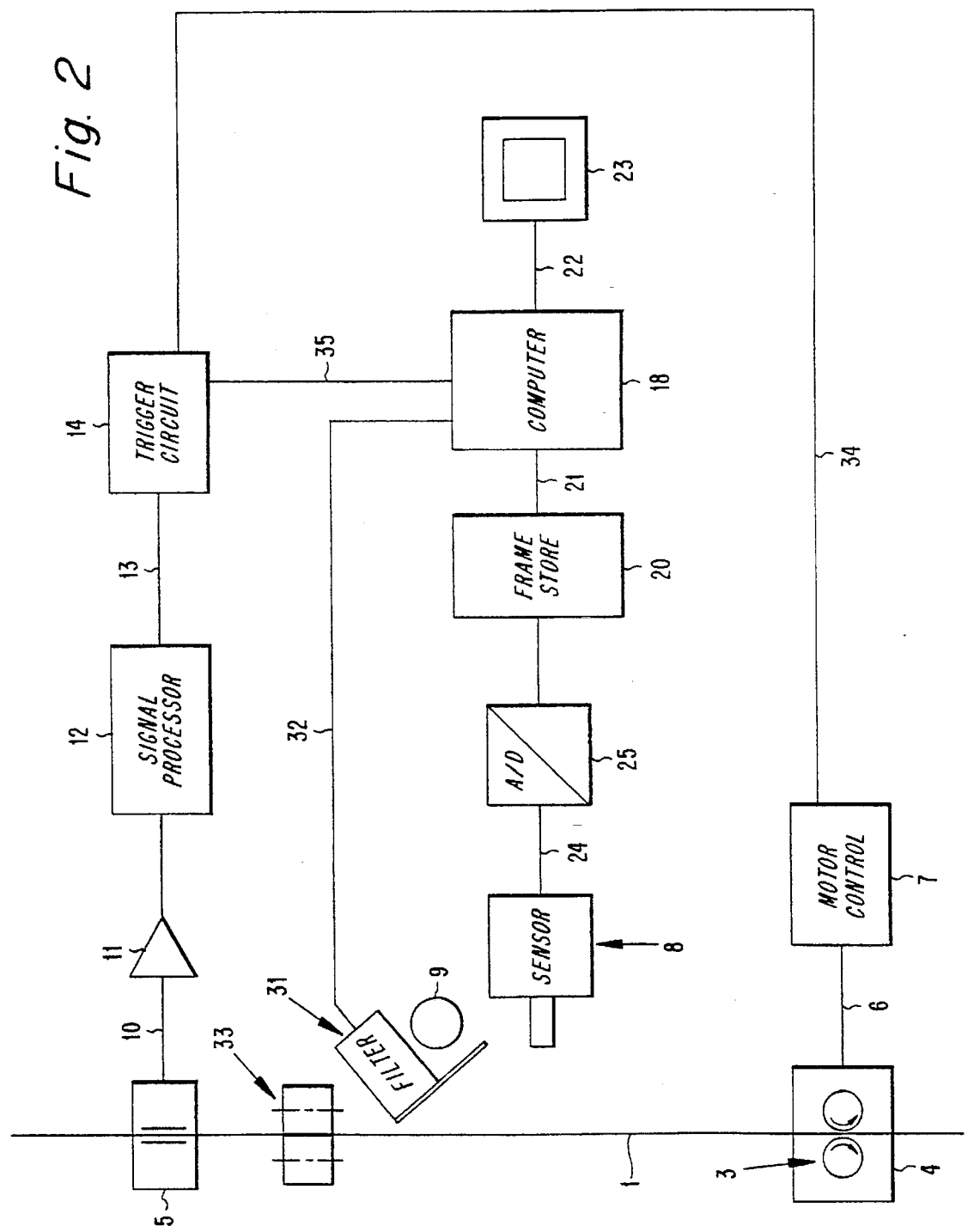
FIG. 2 shows a corresponding representation of a second embodiment.

According to FIG. 2, in which elements corresponding to FIG. 1 are provided with the same reference symbols, the device according to the invention is additionally equipped with a filter unit 31 which is placed in front of the lighting unit 9. The filter unit 31 is connected to the computer 18 via a line 32 and makes it possible to provide special light conditions for the sensor 8. Consequently, for example, a nep analysis or foreign-body analysis can be carried out in different spectral ranges by placing the suitable filter in front. The body 1 can also be twisted or rotated into another position before it comes into the range of the sensor 8. For this purpose, for example, a pair of driven rollers 33 is provided. To this end, if appropriate, the advance of the body 1 can also be switched off briefly, for which purpose the motor control 7 is connected to the trigger 14 via a line 34. Alternatively, here, the trigger circuit is directly connected via a line 35 to the computer 18 which also controls the filter unit 31 via the line 32.

Figure 3:
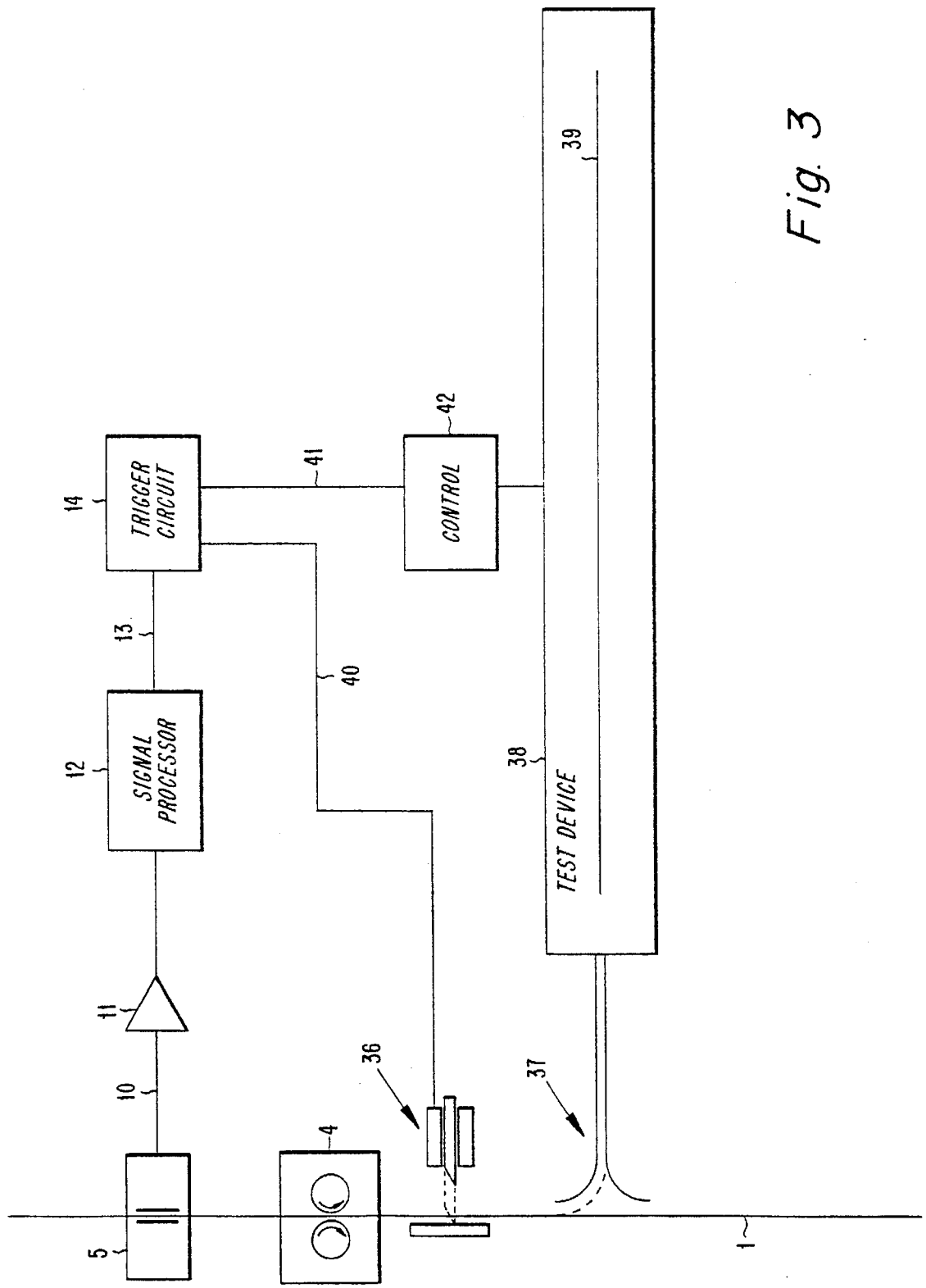
FIG. 3 shows a corresponding representation of a third embodiment.

FIG. 3 shows once again the already known series circuit of the elements 5, 10, 11, 12, 13 and 14 as well as the drive device 4, downstream of which a knife 36 is now arranged. By means of this device, it is possible to extract samples 39 which are separated by the knife 36 and which here are guided, for example via a suction device 37, into a test device 38. Such knives 36 are already known from commercially available yarn clearers. Likewise known are suction devices 37 which are to be encountered in textile machines or laboratory equipment. Lines 40 and 41 connect the trigger circuit 14 on the one hand to the knife 36 and on the other hand to a control 42 for the test device 38. This test device 38 has the function of a further sensor which allows more accurate investigations of the properties of the body. This sensor can be designed, for example, as a tear (or strength) tester such as that disclosed in EP 0 241 894 B1, the disclosure of which is incorporated herein by reference in its entirety. Thus, for example, a thin place can be determined in the sensor 5, a sample having this thin place can then be branched off and this sample be tested for its strength. The tearing strength of this thin place is consequently ascertained, and similar thin places occurring later can be correspondingly treated or evaluated, that is to say left in the body 1 or systematically cut out. Analogous tests can also be carried out along these lines for bodies of a different type in addition to yarns.

Figure 4:
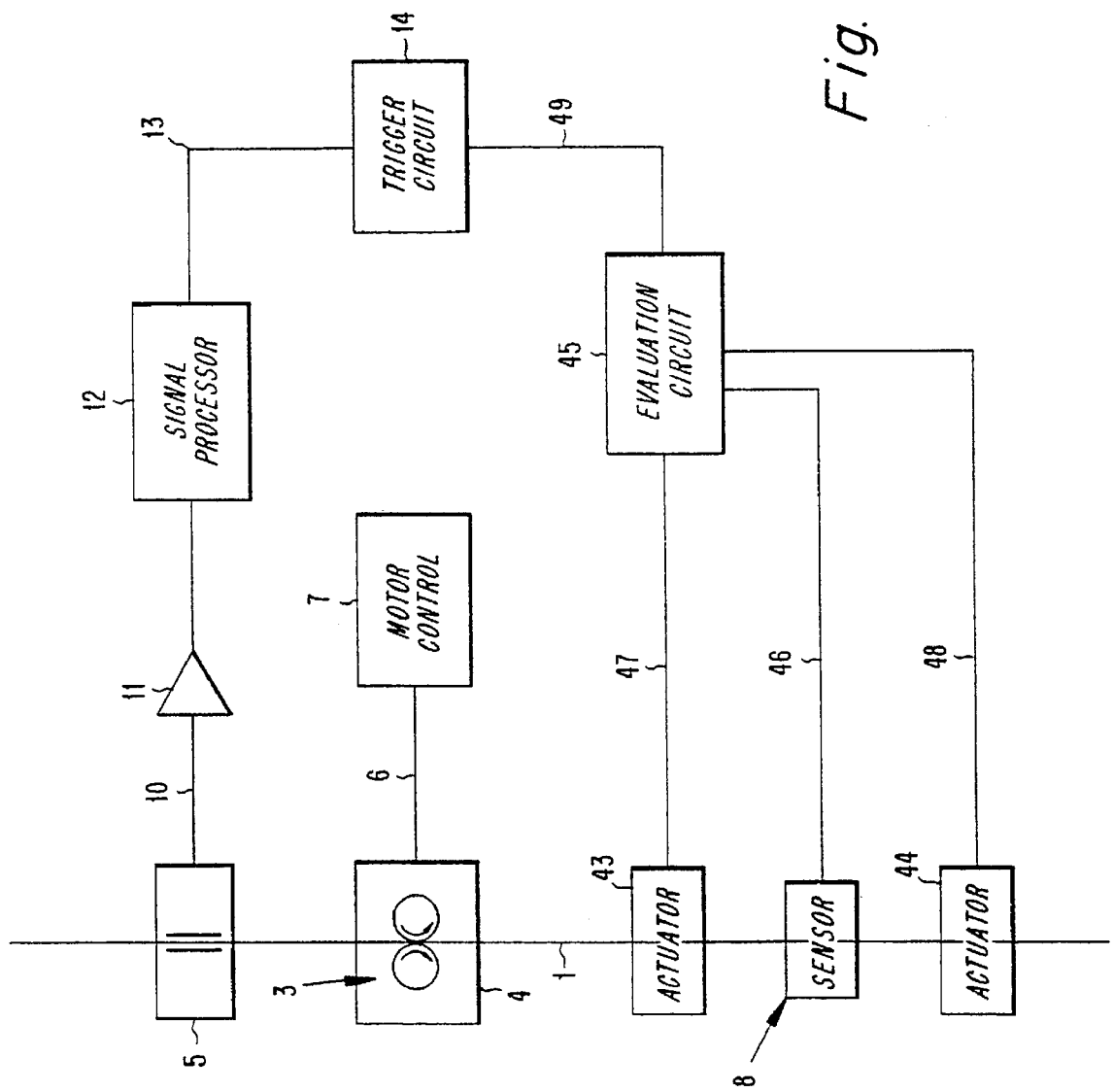
FIG. 4 shows a corresponding representation of a fourth embodiment.

FIG. 4 shows, in addition to the elements 7 already known which cooperate with the sensor 5 and the drive 4, a further sensor 8, actuators 43 and 44 as well as an evaluation circuit 45 which is connected to these via lines 46, 47 and 48. A line 49 connects the evaluation circuit 45 to the trigger circuit 14. The body 1 can be influenced in a specific way by means of the actuators 43 and 44. At the same time, the sensor 8 designed in a correspondingly suitable manner measures the effect achieved. For example, the actuators 43 and 44 can be of the type shown (at 4, 5, 4', 5') in U.S. Pat. No. 5,050,437 and can put the body under tensile stress and a sensor 8 corresponding to the sensor 6 shown in U.S. Pat. No. 5,050,437 measures this stress. The entire disclosure of U.S. Pat. No. 5,050,437 is incorporated herein by reference.

Or, the actuators 43 and 44 may twist the body 1 and the sensor 8 may measure this twist or other quantities which change with the twist, as described in U.S. Pat. No. 5,030,841, the disclosure of which is incorporated herein by reference in its entirety.

Figure 5:
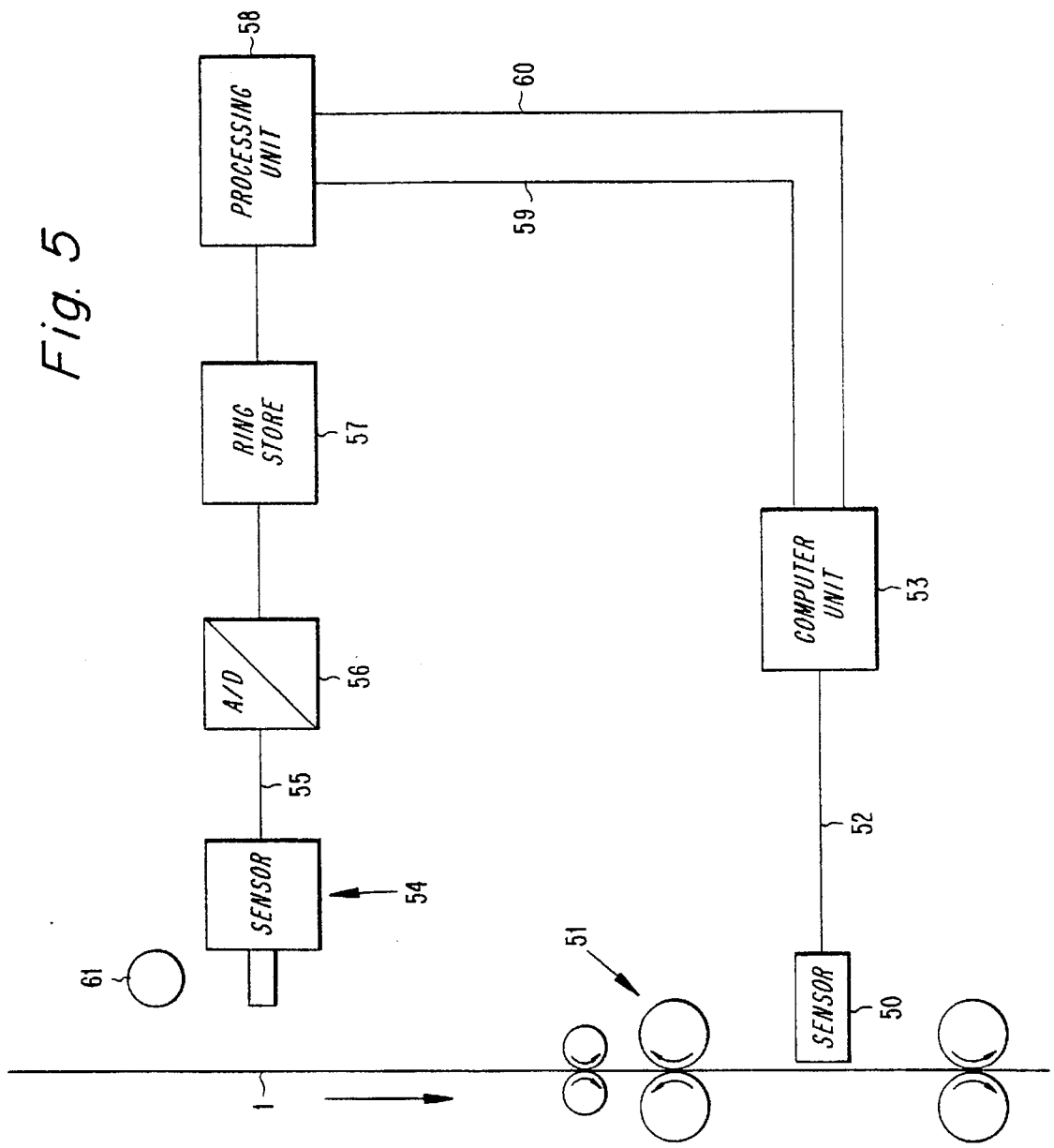
FIG. 5 shows a corresponding representation of a fifth embodiment.

A further version is shown in FIG. 5. In this, a first sensor 50 is integrated, for example, into a continuously working yarn-pull tester 51 (e.g., of the type disclosed in U.S. Pat. No. 5,050,437) which can test the tearing strength of the body 1, here a yarn or a fibre, in a known way. The sensor 50 is connected to a computer unit 53 via a line 52. Provided likewise here as a further sensor 54 is a line-scan camera which is connected via a line 55, an A/D converter 56 and a ring store 57 to a processing unit 58. Lines 59 and 60 connect the latter to the computer unit 53. A lighting unit 61 is also provided in an already known way. In this device, then, the body 1 is first observed continuously by the further sensor 54, in this case being recorded in the form of an image sequence. This image sequence is stored for a predetermined time in the ring store 57 and, when the ring store is filled, is overwritten by more recent images. If, for example, a particularly low value for the tearing strength is determined in the downstream sensor 50, the computer unit 53 can instruct the processing unit 58 via the lines 59 and 60 to remove the images of this yarn sample from the ring store 57 or to interrupt the overwriting in the ring store 57. Thus, this yarn sample can be examined and perhaps an indication as to the cause of the break can be found.

Figure 6:
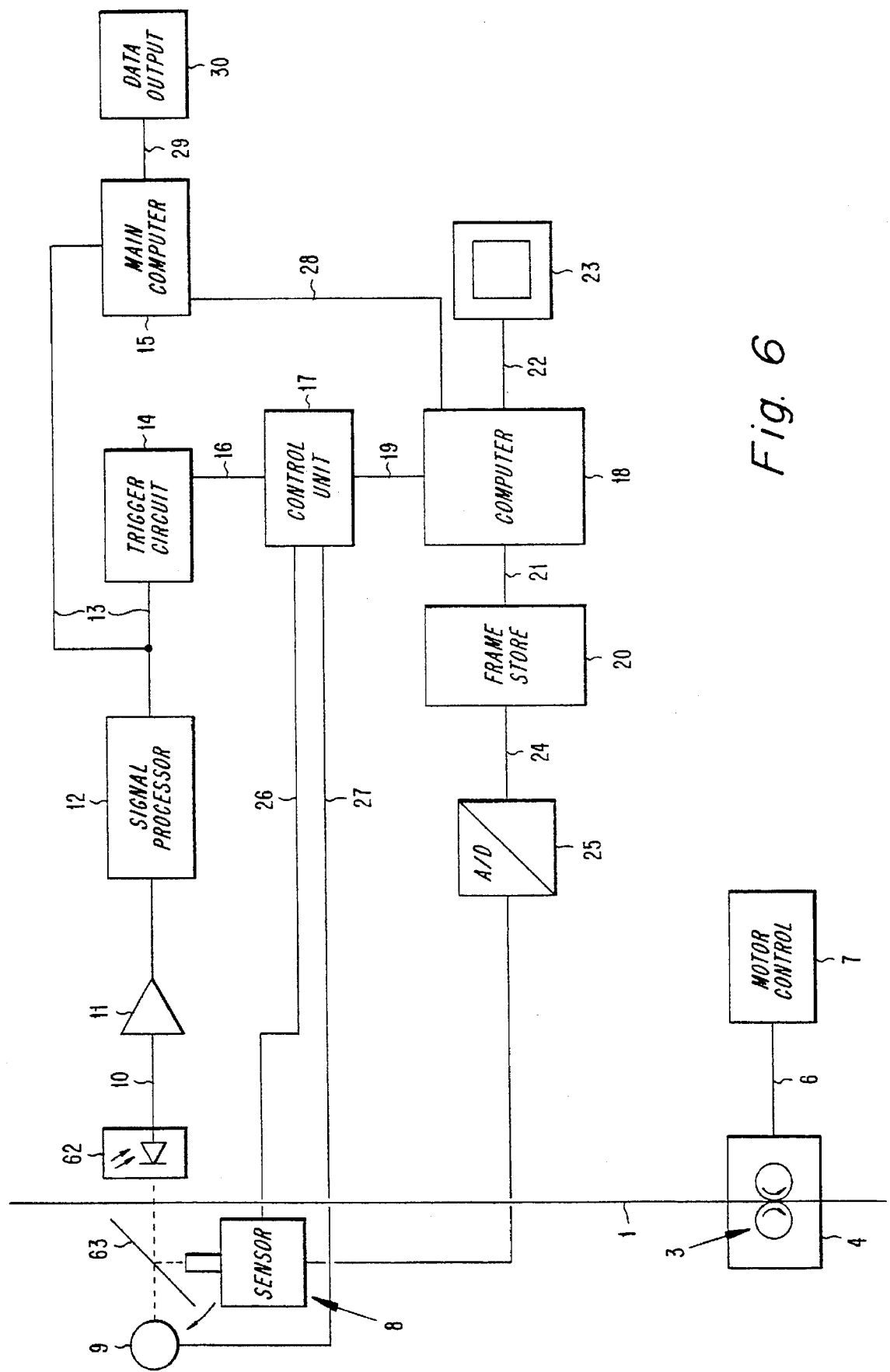
FIG. 6 shows a corresponding representation of a sixth embodiment and FIG. 7 shows a corresponding representation of a seventh embodiment of the device according to the invention.

A further version is shown in FIG. 6. This has for the body 1 an optical sensor 62, here designed as a photodiode, which cooperates with a light source 9 and with a further sensor 8, such as are already known from FIG. 1. The difference from the version according to FIG. 1 is, here, that the light source 9 cooperates, on the one hand, with an optical sensor 62 and, on the other hand, with a camera as a further sensor. A mirror 63, which can be designed as a semi-reflective mirror or which is folded away when the further sensor 8 is activated, makes it possible for the further sensor 8 to be capable of recording the body at the same time and the same location as the first sensor 62. The further elements are already known from FIG. 1 and are also designated identically and therefore are not described any further here.

Figure 7:
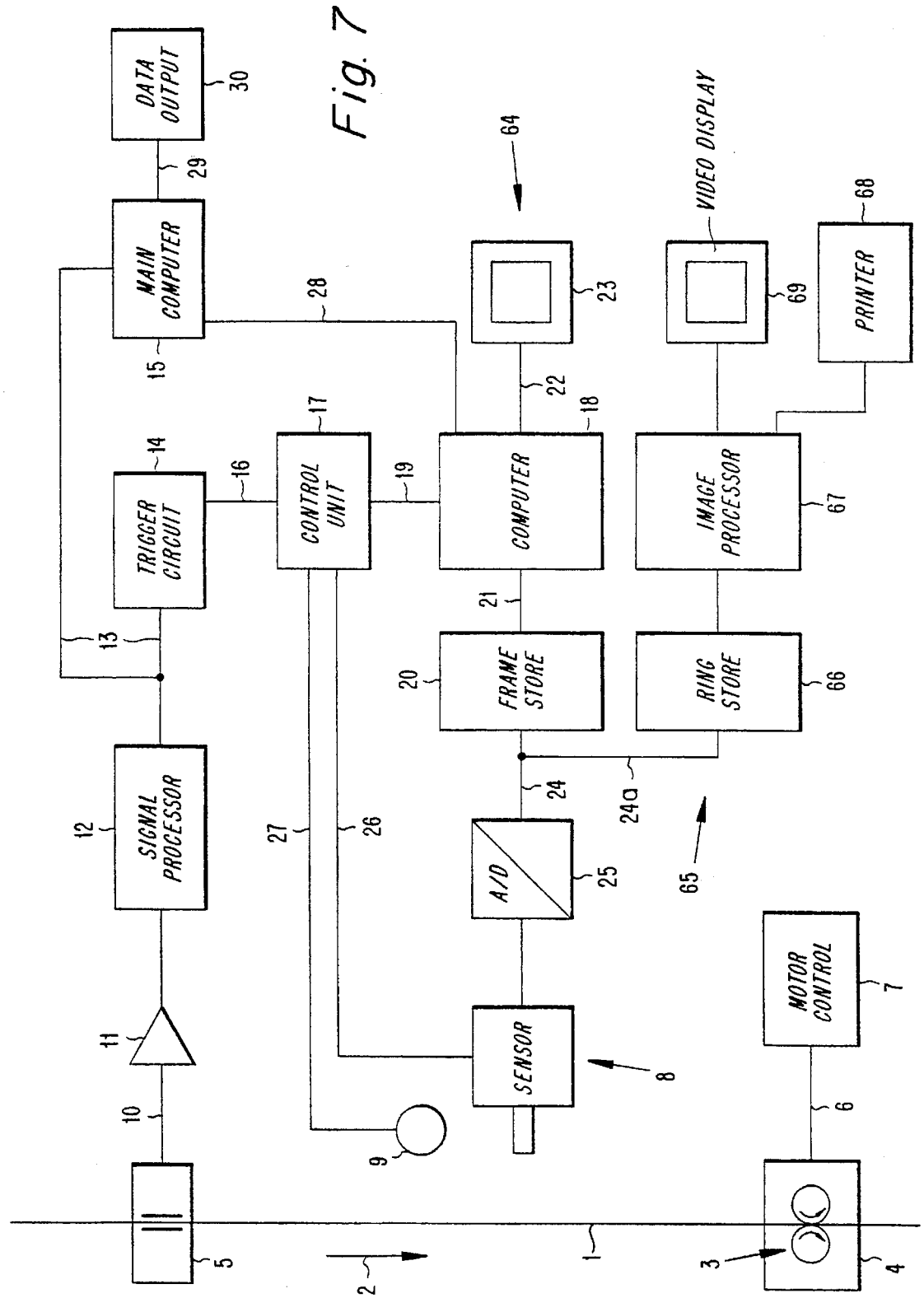

A further alternative differing from the version shown in FIG. 1 is represented in FIG. 7. The same reference symbols are therefore also used for identical elements. In this, two differently designed paths 64 and 65 for processing the signals are provided for the sensor 8. The path 64 has the elements known from FIG. 1 whilst the path 65 has a ring store 66, an image-processing processor 67 (e.g., such as proposed by the company "Imaging Technology, Inc.") and, connected thereto, a printer 68 and/or a video display 69. The ring store 66 is connected to the line 24 via a line 24a and is connected in parallel with the frame store 20. The image-processing processor 67 is connected both to the ring store 66 and to the computer 18. By means of this version, on the one hand, a more detailed examination of the body 1 at points predicted in time and an examination of points on the body which have been indicated as having a time lag can be carried out. If a point of interest is recognized, therefore, on the one hand it can be examined in more detail immediately thereafter, and on the other hand it can also be further consolidated after this more detailed examination when the more detailed examination suggests further investigations.

By means of the devices according to FIGS. 1 to 7, a body can be measured continuously by means of a simple cost-effective sensor. The further, more complicated sensor which works more accurately but more slowly, or else its signal-processing elements, are triggered by the simpler sensor if the latter measures special events. These events are then recorded and stored by the complicated sensor and can subsequently be analyzed accurately in a greater amount of time. The entire time span occurring between two special events can be utilized for this analysis. The two sensors should be synchronized, so that both sensors record the same point in the body. Such a device according to the invention can, in particular, also be adapted to other textile structures, such as bands, nonwovens, etc. This adaptation takes place by the choice of suitable sensors and drive means. The further elements, which are connected to the sensors and which are provided for synchronizing the further sensor and for processing the signals from the sensors, are all elements known per se. The same applies to the programs which are used for evaluating the signals from the more accurately working sensor.

In the textile industry, it is nowadays known to have, for spinning, classification systems laying down criteria according to which irregularities in a yarn can be classified. Such a classification system is referred to in U.S. Pat. No. 5,178,008 (the disclosure of which is incorporated herein by reference) and is widely known under the trademark USTER CLASSIMAT. The simple continuously working sensor can work with such criteria. By means of the further sensor, typical irregularities for each class can be visualized in images whenever they occur. Consequently, the user can obtain a much more detailed picture of the possible type of irregularities which are assigned to a specific class. However, said user can also recognize further particularities in a yarn, such as, for example, fibre loops, projecting ends, the length of the fibres, the orientation of the fibres on the surface, the nappiness or hairiness at close range and at long range, etc. A further possibility is to calculate more accurately, specifically by means of image viewing, the coefficient of variation CV even at very short ranges of, for example, between 0 and 8 mm. By means of this device, dirt particles or foreign bodies in the measured material can also be recognized and be analyzed more accurately. The two sensors can also be combined in such a way that they supply mutually complementary information. For example, the first sensor can work capacitively and thus determine the mass of the body. The second sensor can indicate the diameter of the body by image viewing. By comparison between the mass indication and the diameter, an additional quantity, here the density of the body, can be determined. Further uses not listed here are conceivable. For example, the simpler, continuously working sensor can be arranged on a production machine, such as a cable machine, an extruder for plastic tubes, a spinning machine, a card, etc., and the further, more accurately working sensor can then be arranged remotely relative to the production line, so that the produced material is branched off thereto from time to time for the purpose of carrying out the more accurate measurement.

What is claimed is:

1. Device for sensing and recording a characteristic property of an elongate body which is moved in the longitudinal direction, said device comprising:

a first sensor for sensing and recording first data indicative of said characteristic property to a first degree of accuracy sufficient for routine examination of the elongate body and for generating a trigger signal when said first data indicate an exceptional condition of said characteristic property; and a second sensor responsive to said first sensor for sensing and recording second data indicative of said characteristic property to a second degree of accuracy greater than said first degree of accuracy when triggered by said trigger signal.

2. Device according to claim 1, wherein the first sensor works continuously and employs a first measuring technique, whilst the second sensor works discontinuously and employs a second measuring technique different from said first measuring technique.

3. Device according to claim 1, wherein the second sensor is designed and arranged for recording and processing images.

4. Device according to claim 1, wherein the second sensor is located downstream of the first sensor in the direction of movement of the body.

5. Device according to claim 1, further comprising a data storage device connected to the second sensor for storing said data.

6. Device according to claim 1, second sensor is located upstream of the first sensor in the direction of movement of the body and further comprising a data storage device connected to said second sensor for time-restricted storage of said second data.

7. Device according to claim 1, further comprising a signal conditioning element connected to said second sensor for conditioning of signals generated by said second sensor.

8. Method for recording a characteristic property of an elongate body which is moved in the longitudinal direction, comprising the steps of:

continuously sensing and recording first data indicative of said property of the body using a first measuring technique; and discontinuously sensing and recording second data indicative of said property using a second measuring technique different from said first measuring technique.

9. Method according to claim 8, wherein said first and second measuring techniques are such that said second data are more accurate than said first data.

* * * * *